United States Patent [19]

Martin et al.

[11] Patent Number: 5,583,084
[45] Date of Patent: *Dec. 10, 1996

[54] MULTIMETAL OXIDE COMPOSITIONS

[75] Inventors: Friedrich-Georg Martin, Heidelberg; Hans-Peter Neumann, Mannheim; Hartmut Hibst, Schriesheim, all of Germany

[73] Assignee: BASF Aktiengesellschaft, Ludwigshafen, Germany

[*] Notice: The term of this patent shall not extend beyond the expiration date of Pat. No. 5,521,137.

[21] Appl. No.: 389,197

[22] Filed: Feb. 15, 1995

[30] Foreign Application Priority Data

Feb. 17, 1994 [DE] Germany ............ 44 05 059.3

[51] Int. Cl.⁶ .......................... C07C 51/16; B01J 27/198
[52] U.S. Cl. .................... 502/211; 502/311; 502/220; 562/532
[58] Field of Search ........................ 502/311, 211, 502/220, 209, 212; 562/532

[56] References Cited

U.S. PATENT DOCUMENTS

| | | | |
|---|---|---|---|
| 4,148,757 | 4/1979 | Brazdil et al. | 502/311 |
| 4,212,766 | 7/1980 | Brazdil et al. | 502/311 |
| 4,341,900 | 7/1982 | Ishi et al. | 562/532 |
| 4,469,810 | 9/1984 | Kato et al. | |
| 4,891,347 | 1/1990 | Oh-Kita et al. | 502/200 |
| 4,968,838 | 11/1990 | Oh-Kita et al. | 562/534 |
| 4,985,592 | 1/1991 | Ishii et al. | 562/532 |
| 5,221,767 | 6/1993 | Boehning et al. | 562/532 |
| 5,231,226 | 7/1993 | Hammon et al. | 562/532 |
| 5,364,825 | 11/1994 | Neumann et al. | 502/311 |

FOREIGN PATENT DOCUMENTS

| | | |
|---|---|---|
| 180997 | 5/1986 | European Pat. Off. . |
| 0467144 | 1/1992 | European Pat. Off. . |
| 0534294 | 3/1993 | European Pat. Off. . |
| 0535489 | 4/1993 | European Pat. Off. . |
| 0575897 | 12/1993 | European Pat. Off. . |
| 2302993 | 10/1976 | France . |
| 2610249 | 10/1986 | Germany . |

*Primary Examiner*—Glenn A. Caldarola
*Attorney, Agent, or Firm*—Oblon, Spivak, McClelland, Maier & Neustadt, P.C.

[57] ABSTRACT

Multimetal oxide compositions having a two-phase structure and comprising molybdenum, hydrogen, one or more of the elements phosphorus, arsenic, boron, germanium and silicon, and their use for the preparation of methacrylic acid by gas-phase catalytic oxidation.

18 Claims, No Drawings

MULTIMETAL OXIDE COMPOSITIONS

BACKGROUND OF THE INVENTION

1. Field of the Invention

The present invention relates to multimetal oxide compositions of the formula I $$[A]_p[B]_q \quad (I)$$

where

A is $Mo_{12}X^1_a X^2_b X^3_c X^4_d S_e X^5_f O_x$

B is $X^6_{12} X^7_g X^8_h O_y$ $X^1$ is phosphorus, arsenic, boron, germanium and/or silicon, $X^2$ is vanadium, niobium and/or tungsten, $X^3$ is hydrogen, of which up to 97 mol % may have been replaced by potassium, rubidium, cesium and/or ammonium ($NH_4$), $X^4$ is antimony and/or bismuth, $X^5$ is rhenium and/or rhodium, $X^6$ is molybdenum, tungsten, niobium and/or tantalum, $X^7$ is iron, cobalt, nickel, rhodium, ruthenium, magnesium, calcium, strontium, barium, zinc, cadmium, mercury, yttrium, scandium and/or a rare-earth metal, where, of the latter, cerium, lanthanum and europium are preferred, $X^8$ is lithium, sodium, potassium, rubidium, cesium and/or ammonium ($NH_4$), a is from 1 to 6, preferably from 1 to 3, particularly preferably from 1.5 to 2.5 b is from 0 to 6, preferably from 0.2 to 4, particularly preferably from 0.5 to 2 c is from 3 to 5, d is from 0 to 6, preferably from 0 to 3, particularly preferably from 0.5 to 1.5 e is from 0 to 3, preferably from 0.01 to 1, particularly preferably from 0.01 to 0.2, f is from 0 to 3, preferably from 0.01 to 1, particularly preferably from 0.01 to 0.5, g is from 0.5 to 20, preferably from 4 to 15, particularly preferably from 6 to 12, h is from 0 to 4, preferably from 0.01 to 3, particularly preferably from 0.01 to 2, x and y are numbers determined by the valency and frequency of the elements other than oxygen in I, and p and q are numbers other than zero whose ratio p/q is from 12:0.1 to 12:48, preferably from 12:0.25 to 12:12, particularly preferably from 12:0.5 to 12:4, which contain component $[A]_p$ in the form of three-dimensionally extended regions A of the chemical composition $$Mo_{12}X^1_a X^2_b X^3_c X^4_d S_e X^5_f O_x \quad A$$

which are delimited from their local environment due to their chemical composition which is different from their local environment, and component $[B]_q$ in the form of three-dimensionally extended regions B of the chemical composition $$X^6_{12} X^7_g X^8_h O_y \quad B$$

which are delimited from their local environment due to their chemical composition which is different from their local environment, where the regions A and B are distributed relative to one another as in a finely divided mixture of A and B.

The present invention also relates to a process for the preparation of these compositions, and to their use.

2. Discussion of the Background

DE-A 26 10 249 and EP-A 180 997 relate to multimetal oxide compositions whose empirical elemental composition corresponds to that of the novel multimetal oxide compositions.

These multimetal oxide compositions are prepared by converting suitable sources of the constituents of the desired multimetal oxide compositions in the requisite amounts into an intimate dry mix, and subsequently calcining the latter at elevated temperature for several hours. The resultant multimetal oxide compositions are recommended, inter alia, as catalysts for the preparation of methacrylic acid from methacrolein by gas-phase catalytic oxidation. However, the multimetal oxide compositions of this prior art have the disadvantage that both their activity and the selectivity in the formation of methacrylic acid for a given conversion are not entirely satisfactory. The same applies to the reproducibility of their preparation and to their service lives, which are particularly unsatisfactory if the reaction gases comprising methacrolein as the principal constituent contain organic acids as secondary constituents.

SUMMARY OF THE INVENTION

It is an object of the present invention to provide multimetal oxide compositions which do not have the disadvantages of the multimetal oxide compositions of the prior art.

We have found that this object is achieved by the compositions I defined at the outset. EP-A 835, DEC 338 380, DE--A 42 20 859 and the earlier application DE-A 43 07 380 (O.Z. 0050/43890) likewise relate to multimetal oxide compositions which are suitable as catalysts for the preparation of methacrylic acid from methacrolein by gas-phase catalytic oxidation and which advantageously likewise have a two phase structure, but the elemental composition of the phases of these multimetal oxide compositions of the prior art differs from that of the novel multimetal oxide compositions I.

DESCRIPTION OF THE PREFERRED EMBODIMENTS

Advantageous compositions I are those in which $X^1$ is phosphorus. Favorable compositions I are furthermore those in which $X^2$ is vanadium. It is also advantageous if from 3 to 30 mol % of $X^3$ is potassium, rubidium, cesium and/or ammonium. The preferred hydrogen substitute is cesium. $X^4$ is preferably antimony and $X^5$ is advantageously rhodium. $X^6$ is advantageously molybdenum, and $X^7$ is preferably iron, cobalt or nickel, while $X^8$ is advantageously potassium and/or cesium.

It is furthermore advantageous if at least one of the two components $[A]_p$ and $[B]_q$ in the novel multimetal oxide compositions is in the form of three-dimensionally extended regions having the chemical composition A and B respectively with a maximum diameter $d_A$ or $d_B$ (longest line connecting two points on the surface (interface) of the region and passing through the center of gravity of the region) of >0 to 200 μm, preferably from 1 to 200 μm. The maximum diameter range is very particularly from 1 to 50 μm, particularly advantageously from 1 to 30 μm. It is of course also possible for the maximum diameter to be from 50 to 150 μm or from 75 to 125 μm (the experimental determination of the maximum diameter allows, for example, the method of energy-dispersive X-ray analysis (EXDS), for example using a JEOL JCXA/733 electron beam microprobe).

It is preferred if both component $[A]_p$ and component $[B]_q$ in the novel multimetal oxide compositions are essentially in crystalline form, ie. in general both regions A and regions B essentially comprise small crystallites whose maximum extension is typically from 0.1 to 1 µm.

of a particularly favorable nature are multimetal oxide compositions whose regions A essentially comprise crystallites whose structural type corresponds to that of the ammonium salt of molybdatophosphoric acid $((NH_4)_3PO_4(MoO_3)_{12} \cdot 4H_2O)$. The presence of this crystal structural type can be detected, for example, from the fact that the X-ray diffraction pattern of the novel multi-metal oxide composition contains the diffraction pattern of the ammonium salt of molybdatophosphoric acid (fingerprint), slight differences with respect to the intensity and position of the diffraction lines being possible depending on the elemental composition. The X-ray diffraction fingerprint of the ammonium salt of molybdatophosphoric acid is published, for example, in Card 9–412 of the JCPDS-ICDD Index (1991), which is known and generally accessible to the person skilled in the art. Another source is the National Bureau of Standards (U.S.), Circ. 539, 8 10 (1959). Any antimony in component $[A]_p$ is not, in contrast to the other possible constituents of this component, incorporated into the crystallites containing the molybdatophosphoric acid ammonium salt structural type and is located on the surface of these crystallites or in their interstices. It is advantageous if from 85 to 95% by weight of the antimony is present in the form of senarmontite (a crystalline form of antimony trioxide) in spaces between crystallites of the molybdatophosphoric acid ammonium salt structural type formed essentially from the other elements, while from 5 to 15% by weight is in amorphous solution in the surface of such crystallites (the preparation of multimetal oxide compositions containing senarmontite is given in the earlier application DE-A 43 29 907 (O.Z. 0050/44276).

Preference is furthermore given to multimetal oxide compositions whose regions B essentially comprise crystallites containing a scheelite-related structural type (defect scheelite, either random or with a superstructure; for example of the $Fe_2(MoO_4)_3$ type (cards 31–642 and 35–183 of the JCPDS-ICDD Index (1991)), of the $Bi_2(MoO_4)_3$ type or of the $Eu_2(WO_4)_3$ type). In addition to the defect scheelites, impurities containing scheelite ($CaWO_4$, card 41–1431 of the JCPDS-ICDD Index (1991)), wolframite ($MgWO_4$), distorted wolframite—($CoMoO_4$) or $MnMoO_4$ type can also occur. Particularly suitable here are the high- and low-temperature modifications of $\alpha$-$FeMoO_4$ (card 22–1115 of the JCPDS-ICDD Index (1989, $\beta$-$FeMoO_4$ (card 22–628 of the JCPDS-ICDD Index (1991)), $\alpha$-$CoMoO_4$ and $\beta$-$CoMoO_4$.

The novel compositions I are obtainable in a simple manner, for example, by first forming the oxometallates $$X^6{}_{12}X^7{}_gX^8{}_hO_y \qquad (B)$$

separately in finely divided form (starting composition 1).

The oxometallates B can be prepared by preparing a highly intimate, preferably finely divided, dry mix of suitable sources of their elemental constituents and calcining this dry mix for several hours at from 350° to 500° C. (in principle, it is also possible for the starting composition 1 to be an uncalcined dry mix obtained by spray-drying an aqueous solution or suspension, but the calcined variant is preferred). The calcination can be carried under an inert gas or under a mixture of an inert gas and oxygen (for example air). In general, the calcination time required decreases with increasing calcination temperature. It is essential that the element sources are either already oxides or are compounds which can be converted into oxides by heating, if necessary in the presence of oxygen. Apart from the oxides, suitable starting compounds are therefore in particular halides, nitrates, formates, oxalates, acetates, carbonates and hydroxides. Examples of particularly suitable starting compounds are the following elements:

Mo: ammonium heptamolybdate,

Fe: iron nitrate (aqueous solution),

Co: cobalt nitrate (aqueous solution),

Alkali metal: alkali metal nitrate,

Rh: rhodium chloride,

Re: rhenium pentoxide or ammonium perrhenate.

The intimate mixing of the starting compounds can be carried out in dry or wet form. If it is carried out in dry form, the starting compounds are expediently employed as finely divided powders. However, the intimate mixing is preferably carried out in wet form. In this case, the starting compounds are usually mixed with one another in the form of an aqueous solution and/or suspension. After completion of the mixing operation, the fluid composition is dried and then calcined. The drying is preferably carried out by spray-drying (inlet temperature: 250° to 600° C., outlet temperature: 80° to 130° C.). After calcination, the composition can be comminuted again (for example by wet or dry grinding, for example in a ball mill or by jet grinding), giving a powder generally comprising essentially spherical particles, from which the particle class having a maximum particle diameter in the range desired for the composition I (in general >0 to 200 µm, usually from 1 to 200 µm, preferably from 1 to 50 µm, particularly preferably from 1 to 30 µm) can be separated off by classification in a manner known per se (for example wet or dry screening). The individual powder particle generally comprises numerous crystallites with a maximum extension typically from 0.1 to 1 µm.

A finely divided intimate dry mix is produced in a corresponding manner from sources, suitable in the same way, of the elemental constituents of the oxometallates A $$M_{o12}X^1{}_aX^2{}_bX^3{}_cX^4{}_dS_eX^5{}_fO_x \qquad (A),$$

but this is generally not precalcined (starting composition 2). If the starting composition 2 is employed after prior calcination, the calcination is expediently carried out at from 250° to 450° C. (inert gas, air). Particularly suitable starting compounds are:

Mo: ammonium heptamolybdate,

V: ammonium metavanadate,

P: from 70 to 100%, preferably from 76 to 85%, strength by weight phosphoric acid, Sb: senarmontite, S: ammonium sulfate, Re: rhenium pentoxide or ammonium perrhenate, B: boric acid, As: arsenic trioxide, Si: waterglass, Nb: ammonium niobium oxalate or ammonium niobate, Alkali metals: alkali metal nitrates, $NH_4$: ammonium sulfate, nitrate or carbonate, Bi: bismuth nitrate.

The starting composition 1 and the starting composition 2 are subsequently mixed with one another in the desired mixing ratio in wet or dry form (preferably in dry form), and the mixture is shaped and then calcined for several hours at from 250° to 450° C. The calcination can be carried out under an inert gas, but alternatively under a mixture of inert gas and oxygen, for example air.

The shaping of the mixture of starting composition 1 and starting composition 2 can be carried out by compaction (for example tableting or extrusion), if necessary with addition of conventional auxiliaries, for example graphite or stearic acid as lubricants. In the case of unsupported catalysts, the compaction gives the desired catalyst geometry directly, hollow cylinders having an external diameter and length of from 2 to 10 mm and a wall thickness of from 1 to 3 mm being preferred. Very generally, the mixture of starting composition 1 and starting composition 2 can be shaped either before or after the calcination. This can also be carried out, for example, by comminuting the mixture after the calcination and applying it to inert supports to produce coated catalysts. However, the application can also be carried out before the final calcination. In this case, the application is preferably carried out as described in EP-B 293 859. It is of course also possible to employ the novel compositions I in powder form.

The novel compositions I are particularly suitable as catalysts of increased selectivity for a given conversion, increased activity, extended service life and improved reproducibility in the preparation of methacrylic acid from methacrolein by gas-phase catalytic oxidation.

The catalytic gas-phase oxidation of methacrolein to methacrylic acid using the novel catalysts can be carried out in a manner known per se, for example in the manner described in DE-A 40 22 212.

The same applies to the removal of the methacrylic acid from the product-gas stream. The oxidant oxygen can be employed, for example, in the form of air, but also in pure form.

Owing to the high heat of reaction, the reactants are preferably diluted with an inert gas such as $N_2$, $CO_2$, saturated hydrocarbons and/or steam.

The methacrolein: oxygen: steam: inert gas ratio used is preferably from 1: (1 to 3):(2 to 20):(3 to 30), particularly preferably from 1: (1 to 3):(3 to 10):(7 to 18). The methacrolein employed can have been obtained in various ways, for example by gas-phase oxidation of isobutene, tert-butanol or the methyl ether of tert-butanol. It is advantageous to use methacrolein obtainable by condensation of propanol with formaldehyde in the presence of secondary amines and acids in the liquid phase by the processes described in German Patent 875 114 and in DE-B 28 55 514. The gas-phase oxidation can be carried out either in a fluidized-bed reactor or in a fixed-bed reactor. It is preferably carried out in a tube-bundle reactor whose tubes contain the catalyst composition, in the form of a fixed bed, preferably in the form of cylindrical particles. The reaction temperature is generally from 250° to 350° C., the reaction pressure is usually in the range from 1 to 3 bar, and the overall space-time yield is preferably from 800 to 1800 l (s.t.p.)/l/h. Under these conditions, the methacrolein conversion for a single pass through the reactor is usually from 60 to 90 mol %. Interestingly, the novel compositions retain their properties with virtually no change over an increased operating time.

However, the process described usually does not give pure methacrylic acid, but instead a product mixture from which the methacrylic acid must subsequently be separated off. This can be carried out in a manner known per se, for example by scrubbing the reaction gases at from 40° to 80° C. with water after indirect and/or direct cooling, giving an aqueous methacrylic acid solution, from which the methacrylic acid is usually removed by extraction with an organic solvent and separated therefrom by distillation.

In addition to gas-phase catalytic oxidation of methacrolein to methacrylic acid, the novel compositions I are also capable of catalyzing the gas-phase catalytic oxidation and ammonoxidation of other saturated, unsaturated and aromatic hydrocarbons, alcohols, aldehydes and amines.

Specific mention may be made of the gas-phase catalytic oxidation of other $C_3$–$C_6$-alkanes, alkanols, alkanals, alkenes and alkenols (for example propylene, acrolein, tert-butanol, the methyl ether of tert-butanol, isobutene, isobutane or isobutyraldehyde) to olefinically unsaturated aldehydes and/or carboxylic acids, and the corresponding nitriles (ammonoxidation, in particular of propene to acrylonitrile and of isobutene or tert-butanol to methacrylonitrile). Special mention may be made of the preparation of acrylic acid, acrolein and methacrolein, and the oxidation of n-butane to maleic anhydride and the oxidation of butadiene to furan. However, they are also suitable for the oxidative dehydrogenation of organic compounds.

Conversion, selectivity and residence time in this specification are defined as follows, unless stated otherwise:

$$\text{Conversion } U \text{ of methacrolein (\%)} = \frac{\text{Number of moles of methacrolein reacted}}{\text{Number of moles of methacrolein employed}} \times 100$$

$$\text{Selectivity } S \text{ in the formation of methacrylic acid} = \frac{\text{Number of moles of methacrolein converted into methacrylic acid}}{\text{Number of moles of methacrolein converted in total}} \times 100$$

$$\text{Residence time (sec)} = \frac{\text{Catalyst-filled empty volume of the reactor } (l)}{\text{Amount of synthesis gas passed through } (l(s.t.p.)/h)} \times 3600$$

EXAMPLE a) Preparation of novel multi metal oxide compositions M and multi metal oxide compositions MV for comparison (the contents of hydrogen, ammonium and oxygen in the resultant compositions are determined by by the particular preparation process; the values were not determined regularly and are therefore not present regularly in the stated stoichiometries)

MV1: Example 5 of EP-A 180 997 was repeated. The antimony source used was pure finely divided senarmontite having a number average particle diameter of 0.05 μm. The catalyst geometry selected was hollow cylinders measuring 7 mm (height)×7 mm (external diameter)×3 mm (internal diameter).

The resultant catalyst had the following stoichiometry:

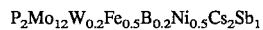

$P_2Mo_{12}W_{0.2}Fe_{0.5}B_{0.2}Ni_{0.5}Cs_2Sb_1$

MV2: Example 14 of DE-A 26 10 249 was repeated (catalyst geometry: 7 mm×7 mm×3 mm hollow cylinders). Resultant catalyst stoichiometry:

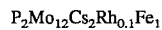

$P_2Mo_{12}Cs_2Rh_{0.1}Fe_1$

M1: Starting composition 2: firstly, 900 g of ammonium heptamolybdate and then 294.5 g of ammonium dodecawolframate and then 165.6 g of cesium nitrate were introduced into 1000 g of water. The temperature of the resultant aqueous mixture was adjusted to from 33° to 40° C. 121.6 g of 76% strength by weight phosphoric acid and 5.8 g of boric acid were stirred into this mixture, and the temperature of the resultant mixture was adjusted to from 37° to 45° C. 68.7 g of finely divided antimony trioxide (pure senarmontite) having a number average particle diameter of 0.05 µm were subsequently added, and the resultant mixture was warmed to 95° C. and kept at this temperature for 1 hour. The aqueous mixture was susbsequently spray-dried at an outlet temperature of 130° C.

The resultant starting composition 2 had the following stoichiometry:

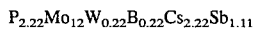

$P_{2.22}Mo_{12}W_{0.22}B_{0.22}Cs_{2.22}Sb_{1.11}$

Starting composition 1: 500 g of water were warmed to 60° C., and 100 g of ammonium heptamolybdate and an aqueous solution of 56.5 g of iron(III) nitrate in 114.5 g of a 12.1% strength by weight aqueous nickel(II) nitrate solution were subsequently added successively, and the resultant mixture was stirred for 2 hours. The aqueous mixture was subsequently spray-dried at an outlet temperature of 140° C., and the spray powder produced was calcined for 6 hours at 460° C. under air.

The resultant starting composition 1 had the following stoichiometry:

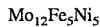

$Mo_{12}Fe_5Ni_5$

Starting composition 2 and starting composition 1 were dry-mixed in a molar ratio of 0.9:0.1. After addition of 3% by weight of graphite, the dry composition was tabletted to give hollow cylinders (7 mm×7 mm×3 mm) and calcined for 10 hours at 400° C. in a stream of air. The stoichiometry of the resultant composition M1 corresponded to that of MV1.

M2: Starting composition 2: starting from ammonium heptamolybdate, cesium nitrate and 76% strength by weight phosphoric acid, a spray powder was produced as for M1 which had the following stoichiometry:

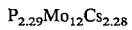

$P_{2.29}Mo_{12}Cs_{2.28}$

Starting composition 1: 600 g of water were warmed to 60° C. and 125 g of ammonium heptamolybdate and a solution of 113.07 g of iron(III) nitrate and 9.88 g of rhodium trichloride in 100 g of water were subsequently added successively, and the resultant mixture was stirred for 2 hours. The aqueous mixture was spray-dried at an outlet temperature of 140° C., and the spray powder produced was calcined for 6 hours at 460° C. under air.

The resultant starting composition 1 had the following stoichiometry:

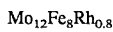

$Mo_{12}Fe_8Rh_{0.8}$

Starting composition 2 and starting composition 1 were dry-mixed in a molar ratio of 0.875/0.125. After addition of 3% by weight of graphite, the dry composition was tabletted to give hollow cylinders (7 mm×7 mm×3 mm) and calcined for 10 hours at 400° C. in a stream of air.

The stoichiometry of the resultant composition M2 corresponded to that of MV2.

M3: Starting composition 2:1000 g of ammonium heptamolybdate, then 55.21 g of ammonium metavanadate and then 128.8 g of cesium nitrate were stirred successively into 1200 g of water. The temperature of the resultant aqueous mixture was adjusted to from 40° to 45° C. 91.29 g of 76% strength by weight phosphoric acid and then 2.49 g of ammonium sulfate were stirred into this mixture, and the temperature of the resultant mixture was adjusted to from 45° to 48° C. 51.6 g of finely divided antimony trioxide (pure senarmontite) having a number average particle diameter of 2.4 µm were then added, and the resultant mixture was warmed to 95° C. and kept at this temperature for 1 hour. The aqueous mixture was subsequently spray-dried at an outlet temperature of 110° C.

The resultant starting composition 2 had the following stoichiometry:

$P_{1.5}Mo_{12}V_1Cs_{1.4}S_{0.04}Sb_{0.75}$

Starting composition 1:166.67 g of ammonium heptamolybdate were dissolved with stirring in 800 g of water kept at 50° C., and a solution of 56.53 g of iron(III) nitrate in 210.95 g of a 12.1% strength by weight aqueous cobalt nitrate solution was subsequently added continuously over the course of 30 minutes, and the resultant mixture was stirred for 3 hours. The aqueous mixture was subsequently spray-dried at an outlet temperature of 140° C. The resultant spray powder was not calcined. It had the following stoichiometry:

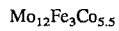

$Mo_{12}Fe_3Co_{5.5}$

Starting composition 2 and starting composition 1 were dry-mixed in a molar ratio of 1:0.17. After addition of 3% by weight of graphite, the dry composition was tabletted to give hollow cylinders (5 mm×5 mm×3 mm) and calcined for 6 hours at 380° C. in a stream of air.

M4: Starting composition: as for M3. Starting composition 1: as for M3, but the spray powder produced was calcined for 6 hours at 460° C. under air.

Starting composition 2 and starting composition 1 were mixed in a molar ratio of 1: 0.17 and converted into hollow-cylindrical catalysts as for M3.

M5: As for M4, but starting composition 2 and starting composition 1 were mixed in a ratio of 1:1.5.

M6: Starting composition 2: as for M4. Starting composition 1: as for M4, with the difference that a corresponding amount of Cs in the form of cesium nitrate was also incorporated. The resultant starting composition 1 had the following stoichiometry:

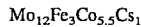

$Mo_{12}Fe_3Co_{5.5}Cs_1$

Starting composition 2 and starting composition 1 were mixed in a molar ratio of 1:0.33 and converted into hollow-cylindrical catalysts as for M3.

M7: Starting composition 2: firstly, 1000 g of ammonium heptamolybdate, then 55.21 g of ammonium metavanadate and then 60% of a solution of 110.24 g of cesium nitrate in 250 g of water were stirred into 1200 g of water. The temperature of the resultant aqueous mixture was adjusted to from 37° to 42° C. 91.29 g of 76% strength by weight phosphoric acid and then 2.49 g of ammonium sulfate were stirred into this mixture, and the temperature of the resultant mixture was adjusted to from 42° to 45° C. 96.31 g of finely divided antimony trioxide (25% of valentinite and 75% of senarmontite) having a number average particle diameter of 3.2 μm were subsequently added, and the mixture was warmed to 95° C. During the heating phase, the remaining 40% of the aqueous cesium nitrate solution, divided into three equal portions, were added when temperatures of 80°, 90° and 95° C. had been reached, each portion being added once. The aqueous mixture was subsequently spray-dried at an outlet temperature of 120° C.

The resultant starting composition 2 had the following stoichiometry:

$$P_{1.5}Mo_{12}V_1Cs_{1.2}S_{0.04}Sb_{1.4}$$

Starting composition 1: as for M4.

Starting composition 2 and starting composition 1 were dry-mixed in a molar ratio of 1:1.5. After addition of 3% by weight of graphite, the dry composition was tabletted to give hollow cylinders (7 mm×5 mm×3 mm) and calcined for 5 hours at 380° C. in a stream of air.

M8: Starting composition 2: the preparation was carried out as for M7, but somewhat less antimony trioxide was added, so that the following stoichiometry was obtained:

$$P_{1.5}Mo_{12}V_1Cs_{1.4}S_{0.04}Sb_{0.75}$$

Starting composition 1: as for M4, but no iron(III) nitrate was used and the cobalt content was increased so that the following stoichiometry was obtained:

$$Mo_{12}Co_{12}$$

Starting composition 2 and starting composition 1 were dry-mixed in a molar ratio of 1: 0.17 and converted into hollow-cylindrical catalysts as for M4.

M9: Starting composition 2: as for M8. Starting composition 1: as for M8, but the cobalt nitrate was replaced by europium(III) nitrate, and the proportion of iron was increased so that the following stoichiometry was obtained:

$$Mo_{12}Fe_7Eu_1$$

Starting composition 2 and starting composition 1 were dry-mixed in a molar ratio of 1:0.33 and converted into hollow-cylindrical catalysts as for M4.

M10: Starting composition 2:1000 g of molybdenumtrioxide and 52.65 g of vanadium pentoxide were suspended in 1000 g of water. 112 g of 76% strength by weight phosphoric acid and 11.35 g of 100% strength by weight sulfuric acid were added to the aqueous suspension. The suspension was subsequently stirred at 95° C., and small amounts of undissolved material were filtered off. The aqueous solution was cooled to 50° C., and 154.2 g of tetrapropylammonium bromide were added continuously over the course of 2 hours. The aqueous mixture was subsequently stirred 50° C. for 4 hours and then spray-dried at an outlet temperature of 110° C. and calcined for 10 hours at 390° C. The resultant starting composition 2 had the following stoichiometry:

$$P_{1.5}Mo_{12}V_1S_{0.2}$$

Starting composition 1: as for M4.

Starting composition 2 and starting composition 1 were dry-mixed in a molar ratio of 1: 0.17. After addition of 3% by weight of graphite, the dry composition was tabletted to give hollow cylinders (7 mm×5 mm×3 mm) and calcined for 5 hours at 380° C. in a stream of air.

M11: Starting composition 2: as for M10, but some of the phosphorus was replaced by arsenic (arsenic(III) oxide), and no sulfuric acid was used. The resultant starting composition 2 had the following stoichiometry:

$$P_{0.5}As_{0.5}Mo_{12}V_1H_4$$

Starting composition 1: as for M4.

Starting composition 2 and starting composition 1 were converted into hollow-cylindrical catalysts as for M4.

b) Use of the multimetal oxide compositions from a) as catalysts for the gas-phase oxidation of methacrolein to methacrylic acid.

The catalysts were introduced into a tubular reactor (internal diameter 10 mm, 100 g of catalyst bed, temperature control by salt bath), and the reactor was charged with a gaseous mixture having the composition 5% by volume of methacrolein, 10% by volume of oxygen, 30% by volume of steam and 55% by volume of nitrogen at a reaction temperature in the range from 280° to 340° C. using a residence time of 3.6 seconds. The salt-bath temperature was essentially set in all cases so that a uniform methacrolein conversion of about 80.5% was obtained. A lower salt-bath temperature indicates an increased catalyst activity. The product-gas mixture flowing out of the reactor was analyzed by gas chromatography. The results for the selectivity of the formation of methacrylic acid using the various catalysts are shown in the table below.

TABLE

| Catalyst | Reaction temperature (°C.) | U (%) | S (%) |
|---|---|---|---|
| MV1 | 340 | 80.1 | 84.9 |
| MV2 | 310 | 84.1 | 85.6 |
| M1 | 305 | 80.1 | 86.3 |
| M2 | 302 | 84.1 | 87.9 |
| M3 | 298 | 81 | 88.8 |
| M4 | 302 | 80.5 | 88.3 |
| M5 | 308 | 81.3 | 87 |
| M6 | 324 | 81.8 | 82.7 |
| M7 | 314 | 80.9 | 87.5 |
| M8 | 322 | 81.2 | 87 |
| M9 | 296 | 81.1 | 88.3 |
| M10 | 283 | 89.8 | 85.4 |
| M11 | 285 | 90 | 86.9 |

Finally, the X-ray diffraction patterns of all multimetal oxide compositions M1 to M11 show both the fingerprint of the ammonium salt of molybdatophosphoric acid $((NH_4)_3PO_4(MoO_3)_{12}\cdot 4H_2O)$ and a defect scheelite fingerprint.

We claim:

1. A multimetal oxide composition of the formula I $$[A]_p[B]_g \qquad (I),$$

where

A is $Mo_{12}X^1_aX^2_bX^3_cX^4_dS_eX^5_fO_x$

B is $X^6_{12}X^7_gX^8_hO_y$ $X^1$ is the sum of phosphorus, arsenic, boron, germanium and silicon, $X^2$ is the sum of vanadium, niobium and tungsten, $X^3$ is hydrogen, of which up to 97 mol % is replaced by potassium, rubidium, cesium and/or ammonium ($NH_4$), $X^4$ is the sum of antimony and bismuth, $X^5$ is the sum of rhenium and rhodium, $X^6$ is the sum of molybdenum, tungsten, niobium and tantalum, $X^7$ is the sum of iron, cobalt, nickel, rhodium, ruthenium, magnesium, calcium, strontium, barium, zinc, cadmium, mercury, yttrium, scandium and a rare-earth metal, $X^8$ is the sum of lithium, sodium, potassium, rubidium, cesium and ammonium ($NH_4$), a is from 1 to 6, b is from 0 to 6, c is from 3 to 5, d is from 0 to 6, e is from 0 to 3, f is from 0 to 3, g is from 0.5 to 20, h is from 0 to 4, x and y are numbers determined by the valency and frequency of the elements other than oxygen in formula I, and p and q are numbers other than zero whose ratio p/q is from 12:0.1 to 12:48, which contains portion $[A]_p$ in the form of three-dimensionally extended regions A which are separated from their local environment due to their chemical composition which is different from their local environment, and portion $[B]_q$ in the form of three-dimensionally extended regions B which are separated from their local environment due to their chemical composition which is different from their local environment, where the regions A and B are distributed relative to one another as in a finely divided mixture of A and B.

2. A multimetal oxide composition as claimed in claim 1, where $X^1$ is phosphorus.

3. A multimetal oxide composition as claimed in claim 1, where $X^2$ is vanadium.

4. A multimetal oxide composition as claimed in claim 1, where from 3 to 30 mol % of $X^3$ is cesium.

5. A multimetal oxide composition as claimed in claim 1, where $X^4$ is antimony.

6. A multimetal oxide composition as claimed in claim 1, where $X^5$ is rhodium.

7. A multimetal oxide composition as claimed in claim 1, where $X^6$ is molybdenum.

8. A multimetal oxide composition as claimed in claim 1, where $X^7$ is iron, cobalt or nickel.

9. A multimetal oxide composition as claimed in claim 1, where $X^8$ is the sum of potassium and cesium.

10. A multimetal oxide composition as claimed in claim 1, where at least one of the two components $[A]_p$ and $[B]_q$ is in the form of three-dimensionally extended regions whose maximum diameter is from 1 to 200 μm.

11. A multimetal oxide composition as claimed in claim 1, where e is from 0.01 to 1.

12. A multimetal oxide composition as claimed in claim 1, whose X-ray diffraction pattern contains the fingerprint of the moybdatophosphoric acid ammonium salt having the structure of $((NH_4)_3PO_4(MoO_3)_{12} \cdot 4H_2O)$.

13. A multimetal oxide composition as claimed in claim 1, where the antimony is in the form of senarmontite.

14. A multimetal oxide composition as claimed in claim 1, whose X-ray diffraction pattern contains a defect scheelite fingerprint.

15. A process for the preparation of a multimetal oxide composition as claimed in claim 1, which comprises preforming an oxometallate B $$X^6{}_{12}X^7{}_gX^8{}_hO_y \qquad B$$

in finely divided form, mixing this with a finely divided, intimate dry mix of sources of the elemental constituents of an oxometaliate A $$Mo_{12}X^1{}_aX^2{}_bX^3{}_cX^4{}_dS_eX^5{}_fO_x,$$

and calcining the mixture at from 250° to 450° C.

16. A process for the preparation of methacrylic acid from methacrolein by gas-phase catalytic oxidation, comprising the step of reacting methacrolein in the presence of a multimetal oxide catalyst wherein said multimetal oxide is a composition of the formula I $$[A]_p[B]_q \qquad (I),$$

where

A is $Mo_{12}X^1{}_aX^2{}_bX^3{}_cX^4{}_dS_eX^5{}_fO_x$

B is $X^6{}_{12}X^7{}_gX^8{}_hO_y$ $X^1$ is the sum of phosphorus, arsenicm, boron, germanium and silicon, $X^2$ is the sum of vanadium, niobium and tungsten, $X^3$ is hydrogen, of which up to 97 mol % is replaced by potassium, rubidium, cesium and/or ammonium ($NH_4$), $X^4$ is the sum of antimony and bismuth, $X^5$ is the sum of rhenium and rhodium, $X^6$ is the sum of molybdenum, tungsten, niobium and tantalum, $X^7$ is the sum of iron, cobalt, nickel, rhodium, ruthenium, magnesium, calcium, strontium, barium, zinc, cadmium, mercury, yttrium, scandium and a rare-earth metal, $X^8$ is the sum of lithium, sodium, potassium, rubidium, cesium and ammonium ($NH_4$), a is from 1 to 6, b is from 0 to 6, c is from 3 to 5, d is from 0 to 6, e is from 0 to 3, f is from 0 to 3 g is from 0.5 to 20, h is from 0 to 4, x and y are numbers determined by the valency and frequency of the elements other than oxygen in formula I, and p and q are numbers other than zero whose ratio p/q is from 12:0.1 to 12:48, which contains portion $[A]_p$ in the form of three-dimensionally extended regions A which are separated from their local environment due to their chemical composition which is different from their local environment, and portion $[B]_q$ in the form of three-dimensionally extended regions B which are separated from their local environment due to their chemical composition which is different from their local environment, where the regions A and B are distributed relative to one another as in a finely divided mixture of A and B.

17. A process as claimed in claim 16, wherein the catalyst is an unsupported catalyst whose geometry is that of a hollow cylinder having an external diameter and a length of from 2 to 10 mm and a wall thickness of from 1 to 3 mm.

18. The multimetal oxide composition as claimed in claim 1, wherein in $X^7$ said rare-earth metal is selected from the group consisting of cerium, lanthanum and europium.

* * * * *